United States Patent
Dilip et al.

(10) Patent No.: US 9,814,680 B2
(45) Date of Patent: Nov. 14, 2017

(54) ANTI-TUBERCULOSIS STABLE PHARMACEUTICAL COMPOSITION IN A FORM OF A DISPERSIBLE TABLET COMPRISING GRANULES OF ISONIAZID AND GRANULES OF RIFAPENTINE AND ITS PROCESS OF PREPARATION

(71) Applicant: SANOFI, Paris (FR)

(72) Inventors: Prajapati Dilip, Gujarat (IN); Prasad Kum, Hyderabad (IN); Khullar Praveen, Dona Paula (IN); Kumar Ramesh, Sheohar (IN); Kumar Shakti, Paris (FR)

(73) Assignee: SANOFI, Paris (FR)

( * ) Notice: Subject to any disclaimer, the term of this patent is extended or adjusted under 35 U.S.C. 154(b) by 108 days.

(21) Appl. No.: 14/906,885

(22) PCT Filed: Jul. 22, 2014

(86) PCT No.: PCT/EP2014/065762
§ 371 (c)(1),
(2) Date: Jan. 21, 2016

(87) PCT Pub. No.: WO2015/011162
PCT Pub. Date: Jan. 29, 2015

(65) Prior Publication Data
US 2016/0184231 A1   Jun. 30, 2016

(30) Foreign Application Priority Data

Jul. 26, 2013 (IN) .......................... 3342/CHE/2013

(51) Int. Cl.
| A61K 9/24 | (2006.01) |
| A61K 31/4409 | (2006.01) |
| A61K 31/496 | (2006.01) |
| A61K 9/00 | (2006.01) |
| A61K 9/20 | (2006.01) |

(52) U.S. Cl.
CPC ............ *A61K 9/209* (2013.01); *A61K 9/0053* (2013.01); *A61K 9/2077* (2013.01); *A61K 9/2095* (2013.01); *A61K 31/4409* (2013.01); *A61K 31/496* (2013.01); *A61K 9/2086* (2013.01)

(58) Field of Classification Search
None
See application file for complete search history.

(56) References Cited

U.S. PATENT DOCUMENTS

| 7,195,769 B2 | 3/2007 | Singh et al. |
| 2003/0072800 A1* | 4/2003 | Singh ..................... A61K 9/209 424/464 |
| 2005/0059719 A1 | 3/2005 | Badawy et al. |
| 2012/0027853 A1* | 2/2012 | Pao ...................... A61K 31/497 424/465 |
| 2016/0158157 A1 | 6/2016 | Dilip et al. |
| 2016/0158226 A1 | 6/2016 | Amith et al. |

FOREIGN PATENT DOCUMENTS

| CN | 1217912 A | 6/1999 |
| CN | 1857280 A | 11/2006 |
| CN | 1989966 B | 6/2011 |
| KR | 2010-0090138 A | 8/2010 |
| WO | WO-02/11728 A2 | 2/2002 |
| WO | WO-02/087547 A1 | 11/2002 |
| WO | WO-2007/043542 A1 | 4/2007 |
| WO | WO-2011/012987 A1 | 2/2011 |
| WO | WO-2012/013756 A2 | 2/2012 |
| WO | WO-2012/013756 A3 | 2/2012 |
| WO | WO-2015/011161 A1 | 1/2015 |
| WO | WO-2015/011163 A1 | 1/2015 |

OTHER PUBLICATIONS

International Search Report dated Oct. 15, 2014, for PCT Application No. PCT/EP2014/065763, filed Jul. 22, 2014, three pages.
International Search Report dated Sep. 25, 2014, for PCT Application No. PCT/EP2014/065761, filed Jul. 22, 2014, four pages.
Written Opinion dated Oct. 15, 2014, for PCT Application No. PCT/EP2014/065763, filed Jul. 22, 2014, six pages.
Written Opinion dated Sep. 25, 2014, for PCT Application No. PCT/EP2014/065761, filed on Jul. 22, 2014, four pages.
U.S. Appl. No. 14/906,876, filed Jul. 22, 2014, also published as US-2016/0158157-A1.
U.S. Appl. No. 14/906,870, filed Jul. 22, 2014, also published as US-2016/0158226-A1.
International Search Report and Written Opinion dated Sep. 25, 2014, for PCT Application No. PCT/EP2014/065762, filed Jul. 22, 2014, 8 pages.
Prasad, B. et al. (Jun. 16, 2006; e-pub. Apr. 18, 2006). "Study of the Interaction Between Rifapentine and Isoniazid Under Acid Conditions," *J. Pharm. Biomed. Anal.* 41(4):1438-1441.
Zumla, A. et al. (Jun. 27, 1998). "Tuberculosis." *BMJ* 316(7149):1962-1964.
Lupin Ltd. (Jan. 2013). Medical Prescription of Akurit Kid Dosage & Drug Information, CIMS India, retrieved from the internet on May 5, 2017, one page.

* cited by examiner

*Primary Examiner* — Susan Tran
(74) *Attorney, Agent, or Firm* — Morrison & Foerster LLP

(57) ABSTRACT

The present invention relates to an oral pharmaceutical fixed dose composition in a form of a dispersible tablet for use in the treatment of tuberculosis, said oral pharmaceutical composition comprising: a) granules comprising isoniazid and at least one intragranular excipient, b) granules comprising rifapentine and at least one intragranular excipient, and c) at least one extragranular excipient, and to its process of preparation.

22 Claims, No Drawings

ANTI-TUBERCULOSIS STABLE PHARMACEUTICAL COMPOSITION IN A FORM OF A DISPERSIBLE TABLET COMPRISING GRANULES OF ISONIAZID AND GRANULES OF RIFAPENTINE AND ITS PROCESS OF PREPARATION

CROSS REFERENCE TO RELATED APPLICATIONS

This application is a National Phase application under 35 U.S.C. §371 of International Application No. PCT/EP2014/065762, filed Jul. 22, 2014, which claims priority benefit to Indian Application No. 3342/CHE/2013, filed Jul. 26, 2013, the disclosures of each of which are herein incorporated by reference in their entirety.

TECHNICAL FIELD OF THE INVENTION

The present invention relates to a chemically stable anti-tuberculosis pharmaceutical fixed dose composition in a form of a dispersible tablet comprising two active principles, namely rifapentine and isoniazid, in separated granules. The invention also provides a process of preparation of such anti-tuberculosis pharmaceutical composition.

BACKGROUND OF THE INVENTION

The infectious disease, tuberculosis (TB), is the leading cause of death worldwide from a single human pathogen, claiming more adult lives than diseases such as acquired immunodeficiency syndrome (AIDS), malaria, diarrhea, leprosy and all other tropical diseases combined (Zumla A, Grange J. B M J (1998) 316, 1962-1964). About one third of the world's population is currently infected with *Mycobacterium tuberculosis* (Mtb), the disease causing agent; 10% of those infected will develop clinical diseases. Although the rate at which people are developing TB has declined, the number of cases continues to increase slowly, according to WHO figures. Hardest hit areas are in the developing world, where poverty, other diseases, and inadequate health care are factors. Killing about 1.6 million people annually, TB is the second leading infectious cause of death worldwide, after HIV/AIDS.

Currently, for effective treatment of TB, a combination of a least the following drugs, isoniazid, rifampin, and pyrazinamide are given to a patient in an initial phase of treatment for 8 weeks, during which the drugs are used in combination to kill the rapidly multiplying population of Mtb as well as to prevent the emergence of drug resistance. This initial phase of treatment is followed by a continuation phase for 24 weeks during which a combination of a least the following drugs isoniazid and rifapentine are given to patients. Such a long combination therapy is not always successful, especially in patients developing drug resistant strains. Also, compliance with the relatively long course of treatment is generally poor. Such non-compliance may lead to treatment failure resulting in development of drug resistance.

In order to control the emergence of drug resistant tuberculosis, the WHO recommends the use of fixed dose combinations (FDC) in the form of tablets which comprise, in the same formulation, two different active principles, namely isoniazid and rifapentine in fixed proportions. FDCs in the form of tablets were previously disclosed.

WO 2007/43542 in the name of SUKA PHARMACEUTICAL CO., LTD discloses a pharmaceutical composition and a kit for tuberculosis treatment. The pharmaceutical composition comprises oxazole compounds, rifapentine and isoniazid, which can be in the form of a tablet.

CN 1717912 in the name of GUANXIN CEN discloses a pharmaceutical composition comprising rifapentine and isoniazid, which can be in the form of a tablet.

CN 185728 in the name of SHUAIHUA MEDICINE SCI TECH CO discloses a sustained release formulation (implant) comprising rifapentine and isoniazid, which can be in the form of a tablet.

However, it is well known by a person skilled in the art that the use of such FDCs may reduce the bioavailability of rifapentine due to an undesirable chemical reaction with isoniazid, especially in the catalytic conditions of the acidic gastric environment (Prasad B. et al. J. Pharm. Biomed. Anal. 2006; 41:1438-1441.).

As such, there remains a need for a stable anti-tuberculosis oral pharmaceutical composition comprising both rifapentine and isoniazid that can prevent the reduction of the bioavailability of the rifapentine and the undesirable chemical reaction with isoniazid.

Applicant has discovered that it was possible to provide such an oral pharmaceutical composition with a satisfactory bioavailability of both active principles by separately granulating the two active principles, and by introducing them in a pharmaceutical composition.

OBJECTS OF THE PRESENT INVENTION

A first object of the present invention is an oral pharmaceutical fixed dose composition in a form of a dispersible tablet for use in the treatment of tuberculosis, said oral pharmaceutical composition comprising:
  a) granules comprising isoniazid and at least one intragranular excipient,
  b) granules comprising rifapentine and at least one intragranular excipient, and
  c) at least one extragranular excipient.

Another object of the present invention is a process for the preparation of an oral pharmaceutical composition according to the present invention, said process comprising distinct steps of granulating isoniazid and granulating rifapentine.

INVENTION

The pharmaceutical composition according to the invention is chemically stable and suitable for the treatment of tuberculosis by oral administration.

By "chemically stable" it is meant that the total amounts of impurities formed from rifapentine is less than 8% w/w with respect to the weight of rifapentine initially present in the tablet and the total amounts of impurities formed from isoniazid is less than 2% w/w with respect to the weight of isoniazid initially present in the tablet, after storage for less than 6 months between 60% RH and 75% RH, at a temperature maintained thermostatically that encompasses the usual and customary working environment from 25° C. to 30° C.

Without being linked by any theory, it is believed that the tablets according to the present invention allow a good availability of both active substances because, due to the particular configuration of the oral pharmaceutical composition, reactions between rifapentine and isoniazid under gastric conditions are limited.

The oral pharmaceutical composition is a fixed dose composition. By "fixed-dose composition" it is meant a combination of two drugs or active ingredients presented in a single dosage unit, i.e. a tablet.

The oral pharmaceutical composition comprises two active principles, namely rifapentine and isoniazid, and pharmaceutically acceptable excipients.

More precisely, the oral pharmaceutical composition comprises granules comprising isoniazid and at least one intragranular excipient (isoniazid granules), granules comprising rifapentine and at least one intragranular excipient (rifapentine granules), and at least one extragranular excipient.

The granules of the oral pharmaceutical compositions exhibit a size less than 0.710 mm as required by US Pharmacopeia for dispersible tablet.

The oral pharmaceutical composition is in a form of a dispersible tablet to facilitate its ingestion, for example, by children. Such dispersible tablet disintegrates into a liquid, for example water, before being administered.

The dispersible tablet can be a dispersible monolayer or a dispersible bilayer tablet.

According to an embodiment where the oral pharmaceutical composition is a dispersible bilayer tablet, one layer of the oral pharmaceutical composition comprises the isoniazid granules and at least one part of the extragranular excipients. The other layer of the oral pharmaceutical composition comprises the rifapentine granules and at least the remaining extragranular excipients.

The extragranular excipients comprise a stabilizer. The stabilizer is selected from the group comprising sodium ascorbate, sodium metabisulphite, di-sodium EDTA, butyl hydroxylated toluene, citric acid, tocopherol, butyl hydroxy anisole, ascorbic acid, tartaric acid, and mixtures thereof. Preferably the extragranular is selected from sodium ascorbate, sodium metabisulphite and mixtures thereof.

The extragranular excipients can also comprise a compound selected from the group comprising a diluent, a disintegrant, a lubricant, a solubilizer, a flavoring agent, a sweetener, a glidant, and mixtures thereof.

As diluent, it can be mentioned microcrystalline cellulose, pregelatinized starch, dicalcium phosphate, mannitol, and mixtures thereof, preferably microcrystalline cellulose.

As disintegrant, it can be mentioned crospovidone (cross-linked polyvinylpyrrolidone), croscarmellose, sodium starch glycollate, maize starch, low substituted hydroxypropylcellulose, alginic acid, preferably crospovidone, sodium starch glycollate and mixture thereof.

As lubricant, it can be mentioned pulverulent lubricant, for example magnesium stearate, sodium sterylfumarate, calcium stearate, stearic acid, zinc stearate, glyceryl behenate and mixtures thereof, preferably calcium stearate, magnesium stearate and mixture thereof.

As solubilizer, it can be mentioned sodium lauryl sulphate, Tween 80, PEG 4000 and mixtures thereof, preferably sodium lauryl sulphate.

As flavoring agent, it can be mentioned mango flavor, orange flavor, cherry flavor, strawberry flavor and mixed fruit flavor.

As sweeteners, it can be mentioned aspartame, sucrose, xylitol and potassium acesulfam, preferably aspartame.

As glidant, it can be mentioned colloidal silicon dioxide, magnesium oxide, magnesium silicate, preferably colloidal silicon dioxide.

According to a specific embodiment, the intragranular excipients present in the isoniazid granules are different from those present in the rifapentine granules.

The intragranular excipient is selected from the group comprising a diluent, a disintegrant, a granulation binder, a stabilizer and mixtures thereof.

The diluent, the disintegrant and the stabilizer are as mentioned above. They can be identical to the diluent, the disintegrant and the stabilizer used as extragranular excipients, or they can be different.

The granulation binder can be selected from povidone, such as povidone K30 or povidone K90, hydroxypropyl cellulose, polyvinyl alcohol, maize starch, pre-gelatinized starch, and mixtures thereof, preferably povidone, or hydroxypropyl cellulose, or pre-gelatinized starch.

The oral pharmaceutical composition according to the present invention may be packed in any suitable packaging, for example in a double aluminium blister packaging thanks to packing machine.

According to an embodiment, the oral pharmaceutical composition comprises from 100 mg to 400 mg of rifapentine and from 40 mg to 400 mg of isoniazid.

The treatment of the tuberculosis is a long time treatment during which the dosage regimen varies. For example, a common prescribed dosing is 600 mg twice weekly for two months, with an interval of no less than 3 consecutive days (72 hours) between doses, in combination with other anti-tuberculosis drugs up to 2 months for the initial phase of TB treatment. Said 2 months phase with 600 mg once weekly is followed by a 4 months phase by direct observation therapy with isoniazid or another appropriate antituberculous agent. A common prescribed dosing for Isoniazid is 5 mg/kg up to 300 mg daily in a single dose and 15 mg/kg up to 900 mg/day, two to three times/week.

Due to said type of treatment, it is very useful that different tablets are available which differ from one to the other one by the ratios rifapentine/izoniazid.

According to an embodiment, the ratio of rifapentine to isoniazid is comprised from 3:1 to 1:0.5, preferably the ratio of rifapentine to isoniazid is 1:1.

More specifically, tablets according to the invention can contain 150 mg of rifapentine and 150 mg of isoniazid, 120 mg of rifapentine and 50 mg of isoniazid, 90 mg of rifapentine and 50 mg of isoniazid.

According to a preferred embodiment where the stabilizer is sodium ascorbate, the ratio of sodium ascorbate to rifapentine is comprised from 1:100 to 1:0.1, preferably from 1:40 to 1:20, more preferably is from 1:35 to 1:25, and even more preferably is 1:30.

The percentages are expressed in weight with respect to the total weight of the tablet.

According to an embodiment, the oral pharmaceutical composition comprises:
from 5% to 50%, preferably from 10% to 30%, and even more preferably from 14% to 22% of rifapentine, and
from 5% to 50% preferably from 7.5% to 30%, and even more preferably from 9% to 17% of isoniazid.

According to an embodiment, the oral pharmaceutical composition comprises from 0.1% to 80%, preferably from 20% to 70%, and more preferably from 40% to 60% of diluent.

According to an embodiment, the oral pharmaceutical composition comprises from 0.1% to 50%, preferably from 1% to 40%, and more preferably from 1.5% to 25% of disintegrant.

According to an embodiment, the oral pharmaceutical composition comprises from 0.1% to 10%, preferably from 1% to 7.5%, and more preferably from 1.25% to 5% of binder.

According to an embodiment, the oral pharmaceutical composition comprises from 0.1% to 1%, preferably from 0.2% to 0.8%, and more preferably from 0.4% to 0.6% of lubricant.

According to an embodiment, the oral pharmaceutical composition comprises less than 2%, preferably less than 1.5%, and more preferably less than 1% of solubilizer.

According to an embodiment, the oral pharmaceutical composition comprises from 0.1% to 2%, preferably from 0.2% to 1.5%, and more preferably from 0.5% to 0.9% of stabilizer.

According to an embodiment, the oral pharmaceutical composition comprises less than 2%, preferably less than 1.5%, and more preferably less than 1.1% of glidant.

According to an embodiment, the oral pharmaceutical composition comprises from 0.1% to 5%, preferably from 0.5% to 3%, and more preferably from 0.9% to 2% of flavoring agent.

According to an embodiment, the oral pharmaceutical composition comprises from 0.1% to 5%, preferably from 0.25% to 4%, and more preferably from 0.4% to 3% of sweetener.

According to an embodiment, the oral pharmaceutical composition in a form of a dispersible tablet is characterized by a hardness from 50 N to 200 N, preferably from 75 N to 175 N, and more preferably from 100 N to 160 N.

The hardness is measured on a Hardness Tester. A tablet is placed between two arms, one arm is static and the other arm pushes the tablet against the static arm to crush the tablet. The pressure applied to crush the tablet is reported by the apparatus. The values are reported in Newtons or Kilopascals According to an embodiment, the oral pharmaceutical composition in a form of a dispersible tablet is characterized by a friability less than 5%, preferably less than 2.5% and more preferably less than 1%.

The friability is measured on a standard equipment known as a Friabilator. 20 tablets are weighed and loaded in the apparatus (or 6 grams of tablets are loaded in apparatus). The apparatus is then rotated for 100 revolutions at 25 RPM/Min. The tablets are unloaded and weighed. The % friability is determined by the formula: [(Weight of tablets before rotations−Weight of tablets after rotations)/Initial weight]×100.

According to an embodiment, the oral pharmaceutical composition in a form of a dispersible tablet is characterized by a disintegration time of said dispersible tablet in water at 25° C. of less than 5 minutes, preferably less than 3 minutes and more preferably less than 2 minutes.

The disintegration time is measured in 900 mL of purified water. The temperature is maintained at 25° C. The disintegration time apparatus consists of 6 tubes with a 2 mm sieve at the bottom of each tube, which are operated at 30 dips/min. One tablet is placed in each tube, and the apparatus is operated until the complete mass of the tablet breaks/disintegrates i.e. passes through the 2 mm sieve.

According to another object, the invention relates to a process for the preparation of the oral pharmaceutical composition comprising distinct steps of granulating isoniazid and granulating rifapentine.

According to a specific embodiment, the process for the preparation of a monolayer tablet comprises the steps of:
a) preparing the isoniazid granules,
b) preparing the rifapentine granules,
c) mixing the granules obtained from steps a) and b) with the extragranular excipients, and
d) compressing the mixture of step c) to obtain tablets.

The distinct steps of granulating are performed by wet granulation.

The wet granulation is performed with a granulation composition which can be an aqueous solvent, a liquid binder, an organic solvent, such as isopropyl alcohol, acetone and chloroform, preferably an aqueous solvent. Said granulation composition can also comprise a binder, a diluent, a disintegrant or mixtures thereof.

After wet granulation, the granules are dried. They can be sifted to improve and enhance the dryness The granules can then be sieved to obtain homogenous granules size and to select granules whose size is less than 1.5 mm, preferably less than 1 mm and more preferably less than 0.710 mm to be homogeneously mixed.

All the extragranular excipients are mixed together, except the lubricant which is incorporated at the end of the mixing.

Before compression, the mixture can be sieved in order to have homogeneous size particles and thus to facilitate the compression.

According to a specific embodiment, the process for the preparation of a bilayer tablet comprises the steps of:
a) preparing a layer comprising the isoniazid granules and at least a part of the extragranular excipients,
b) preparing a layer comprising the rifapentine granules and the remaining part of the extragranular excipients,
e) compressing the layer of step a) and the layer of step b) to obtain bilayer tablets.

The specificities of the different steps described above for the monolayer tablets apply also for the bilayer tablets.

The step of preparing a layer comprises preparing the granules of active principle, then mixing them with the extragranular excipients, followed by a sieving. The present invention will be described with more details in the following examples which are provided for illustrative purposes only.

EXAMPLES

Example 1

Composition of Dispersible Bilayer Tablets

| | Qty (mg/tablet) | Function |
|---|---|---|
| Layer with rifapentine granules Intra-granular excipients | | |
| rifapentine | 150.00 | active |
| microcrystalline cellulose | 63.75 | diluent |
| sodium starch glycollate | 5.00 | disintegrant |
| pre-gelatinized starch | 20.00 | binder |
| purified water* | q. s | granulation fluid |
| Extra-granular excipients | | |
| microcrystalline cellulose | 246.25 | diluent |
| sodium ascorbate | 5.00 | stabilizer |
| sodium starch glycollate | 5.00 | disintegrant |
| sodium lauryl sulphate | 2.50 | solubilizer |
| calcium stearate | 2.50 | lubricant |
| Layer with isoniazid granules Intra-granular excipients | | |
| isoniazid | 150.00 | active |
| microcrystalline cellulose | 40.00 | diluent |
| sodium starch glycollate | 2.00 | disintegrant |
| povidone K30 | 10.00 | binder |
| purified water* | q. s | granulation fluid |
| Extra-granular excipients | | |
| sodium starch glycollate | 4.00 | disintegrant |
| microcrystalline cellulose | 166.50 | diluent |
| mango flavor | 18.00 | flavoring agent |
| aspartame | 27.00 | sweetener |
| calcium stearate | 2.50 | lubricant |
| Total (tablet weight) | 920.00 | |

*Removed during drying, does not appear in the final product except in traces.

Process of Preparation of the Dispersible Bilayer Tablets

The microcrystalline cellulose, pre-gelatinized starch and sodium starch glycollate are separately sifted through, respectively, 0.425 mm, 0.250 mm and 0.180 mm sieve. These materials are then co-sifted with rifapentine through 0.500 mm sieve.

Theses sifted materials are then dry mixed in a rapid mixer granulator for 20 min at 100 rpm.

They are then granulated in a rapid mixer granulator using purified water initially at 125 rpm and chopper at 1000 rpm for 3 min and 30 seconds. The same blend is further kneading at 150 rpm and chopper at 1000 rpm for 6 min to get the granules of desired consistency.

The obtained wet granules are then dried in a fluid bed dryer at inlet temperature from 60° C. to 70° C. for 4.75 hours. The resulting dried granules are next sifted through a 0.600 mm sieve to select the sifted dried granules having a size less than 0.710 mm.

Sodium ascorbate and sodium starch glycollate are sifted through 0.180 mm sieve, microcrystalline cellulose and sodium lauryl sulphate are sifted through 0.425 mm sieve. These sifted materials are then blended with the selected sifted dried granules in a double cone blender for 25 min. at 18 rpm speed.

Finally, this blend is lubricated using calcium stearate (sieved through 0.250 mm sieve) for 5 min in double cone blender 18 rpm speed.

The microcrystalline cellulose and sodium starch glycollate are firstly sieved through, respectively, 0.425 mm sieve and 0.180 mm sieve. These materials are then co-sifted with isoniazid through 0.425 mm sieve, then dry mix in a rapid mixer granulator for 15 min. This resulting blend is granulated using a solution of povidone K30 dissolved in purified water in a rapid mixer granulator initially at 100 rpm for 2 min. The same blend is further kneading at 125 rpm and chopper at 1000 rpm for 1.5 min to get the granules of desired consistency The obtained wet granules are then dried in a fluid bed dryer at inlet temperature from 45° C. to 50° C. for 15 min. The resulting dried granules are then sifted through a 0.600 mm sieve to select the dried granules having a size less than 0.710 mm.

Sodium starch glycollate and mango flavor are sieved through 0.180 mm, microcrystalline cellulose and aspartame are sifted through 0.425 mm sieve. These sifted materials are then blended in double cone blender with the previously selected dried granules for 15 min at 18 rpm speed.

Finally, this blend is lubricated using calcium stearate (sieved through 0.250 mm sieve) for 5 min in double cone blender 18 rpm speed.

The bilayer tablet is obtained by introducing successively the first blend in the first layer hopper and then the second one in the second layer hopper and compressed as bi-layered tablets using the 15.5 mm flat face bevelled edged tooling to obtain the bi-layered tablet of 5.0 mm thickness Its hardness is equal to 150 N and its disintegration time is 30 seconds.

Finally the dispersible bilayer tablet is packed in alu-alu blister.

Stability Data Study of the Packed Dispersible Bilayer Tablets

The packed coated bilayer tablets were subjected to a stability study at accelerated [40° C./75% RH] and real time condition [25° C./60% RH and 30° C./75% RH]. Analysis by HPLC method was carried just after manufacture (initial), at 3 months and at 6 months. The analysis by HPLC method leads to the total amount of impurities for both rifapentine and isoniazid related substances.

Table 1 presents the results of the degradation of rifapentine and isoniazid under these conditions. The results indicated that the total amount of impurities for both rifapentine and isoniazid related substances are below the specification.

TABLE 1

Amount of impurities from rifapentine and isoniazid

| Product Name: Rifapentine & Isoniazid Dispersible Tablets 150/150 mg Pack Alu-Alu Blister | | | 40° C. + 75% RH | | 25° C./60% RH | | 30° C./75% RH | |
|---|---|---|---|---|---|---|---|---|
| | Specification | Initial | 3 Month | 6 Month | 3 Month | 6 Month | 3 Month | 6 Month |
| Related Substances - Rifapentine | | | | | | | | |
| MDL 13437(Rifapentine Demetil) | 1.00 | 0.047 | 0.192 | 0.185 | 0.099 | 0.127 | 0.143 | 0.172 |
| MDL 46,863 (Rifapentine N-oxide) | 1.50 | 0.290 | 0.927 | 1.023 | 0.608 | 0.832 | 0.775 | 1.011 |
| MDL 27,718 (25-Desacetyl Rifapentine) | 0.25 | 0.027 | 0.049 | 0.069 | 0.037 | 0.042 | 0.049 | 0.083 |
| MDL 63,746 (3 formyl Rifamycin SV) | 0.80 | 0.073 | 0.201 | ND | 0.137 | 0.203 | 0.160 | 0.159 |
| MDL 105929 (Rifapentine Quinone) | 3.00 | 0.657 | 2.558 | 2.386 | 1.782 | 2.342 | 2.240 | 2.607 |
| Rifapentine + INH Adduct | 4.00 | 0.149 | 0.144 | 0.134 | 0.086 | 0.152 | 0.102 | 0.174 |
| Single Max Unknown-1 | 0.50 | 0.223 | 0.240 | 0.232 | 0.212 | 0.167 | 0.216 | 0.206 |
| Total Impurities | 8.00 | 2.192 | 6.257 | 5.390 | 4.201 | 5.173 | 5.204 | 5.993 |
| Related Substances - Isoniazid | | | | | | | | |
| Single Max Unknown | 0.30 | 0.061 | 0.099 | 0.119 | 0.057 | 0.107 | 0.106 | 0.115 |
| Total Impurities | 2.00 | 0.138 | 0.231 | 0.456 | 0.162 | 0.357 | 0.244 | 0.404 |

Example 2

Composition of Dispersible Monolayer Tablets

| | Qty (mg/tablet) | Function |
|---|---|---|
| Intra-granular excipients Rifapentine granules | | |
| rifapentine | 150.00 | active |
| microcrystalline cellulose | 15.00 | diluent |
| sodium ascorbate | 2.50 | stabilizer |
| hydroxypropyl cellulose | 7.50 | binder |
| purified water* | q.s | granulation fluid |

-continued

|  | Qty (mg/tablet) | Function |
|---|---|---|
| *Isoniazid granules* | | |
| isoniazid | 150.00 | active |
| microcrystalline cellulose | 15.00 | diluent |
| povidone K30 | 7.50 | binder |
| purified water* | q.s | granulating fluid |
| *Extra-granular excipients* | | |
| microcrystalline cellulose | 385.00 | diluent |
| crospovidone | 125.00 | disintegrant |
| sodium starch glycollate | 125.00 | disintegrant |
| sodium ascorbate | 2.50 | stabilizer |
| aspartame | 5.00 | sweetener |
| mango flavor | 10.05 | flavoring agent |
| colloidal silicone dioxide | 10.00 | glidant |
| magnesium stearate | 5.00 | lubricant |
| Total (tablet weight) | 1015.05 | |

*Removed during drying, does not appear in the final product except in traces.

Process of Preparation of the Dispersible Monolayer Tablets

The granules are prepared as disclosed in example 1 but using the constituents mentioned in the above table.

The rifapentine and isoniazid selected dried granules are firstly blended with the extra-granular excipients: microcrystalline cellulose, crospovidone, sodium ascorbate, sodium starch glycollate, aspartame and mango flavor. The resulting blend is then lubricated using colloidal silicon dioxide and magnesium stearate. Finally, the lubricated blend is compressed into the tablets.

The dimensions of the resulting dispersible monolayer tablet are respectively 20 mm×10 mm×6.34 mm. Its hardness is equal to 155 N and its disintegration time is 100 seconds.

The packed dispersible monolayer tablets were subjected to a stability study as in example 1. Table 2 presents the degradation of rifapentine and isoniazid under these conditions. The results indicated that the total impurities for both rifapentine and isoniazid related substances are below the specification.

The invention claimed is:

1. An oral pharmaceutical fixed dose composition for the treatment of tuberculosis, wherein the oral pharmaceutical fixed dose composition is in the form of a dispersible bilayer tablet consisting essentially of:
    a) isoniazid layer comprising isoniazid granules and at least one intragranular excipient;
    b) rifapentine layer comprising rifapentine granules and at least one intragranular excipient; and
    c) at least one extragranular excipient;
    wherein the ratio of rifapentine to isoniazid is from 3:1 to 1:0.5.

2. The oral pharmaceutical fixed dose composition according to claim 1, wherein the oral fixed dose pharmaceutical composition is chemically stable.

3. A process for preparing the oral pharmaceutical fixed dose composition according to claim 1, comprising distinct steps of granulating isoniazid and granulating rifapentine.

4. The process according to claim 3, wherein the isoniazid granules and the rifapentine granules are made by wet granulation.

5. The process according to claim 3, comprising the steps of:
    a) preparing the isoniazid granules;
    b) preparing the rifapentine granules;
    c) mixing the isoniazid granules and the rifapentine granules obtained from steps a) and
    b) with the at least one extragranular excipient to form a mixture; and
    d) compressing the mixture obtained from step c) to obtain a dispersible tablet.

6. The process according to claim 3, comprising the steps of:
    a) preparing the isoniazid granules;
    b) mixing the isoniazid granules obtained from step a) with at least one portion of the at least one extragranular excipient to form a first mixture;
    c) preparing the rifapentine granules;
    d) mixing the rifapentine granules obtained from step c) with a second portion of the at least one extragranular excipient to form a second mixture; and
    e) compressing the first mixture of step b) and the second mixture of step d) to obtain a dispersible bilayer tablet.

TABLE 2

Amount of impurities from rifapentine and isoniazid

Product Name: Rifapentine & Isoniazid Dispersible Tablets 150/150 mg Pack Alu-Alu Blister

| | | | 40° C./75% RH | | 25° C./60% RH | | 30° C./75% RH | |
|---|---|---|---|---|---|---|---|---|
| | Specification | Initial | 3 Month | 6 Month | 3 Month | 6 Month | 3 Month | 6 Month |
| *Related Substances - Rifapentine* | | | | | | | | |
| MDL 13437(Rifapentine Demetil) | 1.00 | 0.034 | 0.121 | 0.115 | 0.066 | 0.066 | 0.099 | 0.108 |
| MDL 46,863 (Rifapentine N-oxide) | 1.50 | 0.273 | 1.027 | 0.932 | 0.591 | 0.582 | 0.882 | 0.868 |
| MDL 27,718 (25-Desacetyl Rifapentine) | 0.25 | 0.039 | 0.026 | 0.026 | 0.032 | 0.032 | 0.026 | 0.026 |
| MDL 63,746 (3 formyl Rifamycin SV) | 0.80 | 0.056 | 0.058 | 0.024 | 0.072 | 0.039 | 0.071 | 0.030 |
| MDL 105929 (Rifapentine Quinone) | 3.00 | 0.111 | 0.094 | 0.074 | 0.169 | 0.116 | 0.231 | 0.124 |
| RPT + INH adduct | 4.00 | 0.068 | 1.244 | 1.923 | 0.420 | 0.522 | 0.759 | 0.981 |
| Single Max Unknown | 0.50 | 0.262 | 0.234 | 0.275 | 0.256 | 0.234 | 0.250 | 0.217 |
| Total Impurities | 8.00 | 1.367 | 4.694 | 5.355 | 2.704 | 2.723 | 3.847 | 4.040 |
| *Related Substances - Isoniazid* | | | | | | | | |
| Single Max Unknown | 0.30 | 0.109 | Not analysed | 0.289 | Not analysed | 0.105 | Not analysed | 0.196 |
| Total Impurities | 2.00 | 0.342 | Not analysed | 1.090 | Not analysed | 0.499 | Not analysed | 0.844 |

7. The oral pharmaceutical fixed dose composition according to claim 1, wherein the ratio of rifapentine to isoniazid is 1:1.

8. The oral pharmaceutical fixed dose composition according to claim 1, wherein the ratio of rifapentine to isoniazid is 1:1.

9. The process of claim 3, wherein the ratio of rifapentine to isoniazid is 1:1.

10. The process of claim 5, wherein the ratio of rifapentine to isoniazid is 1:1.

11. The process of claim 6, wherein the ratio of rifapentine to isoniazid is 1:1.

12. The process of claim 4, wherein the isoniazid granules and the rifapentine granules are made by wet granulation in an aqueous solvent.

13. The process of claim 5, wherein the isoniazid granules and the rifapentine granules are made by wet granulation.

14. The process of claim 13, wherein the isoniazid granules and the rifapentine granules are made by wet granulation in an aqueous solvent.

15. The process of claim 6, wherein the isoniazid granules and the rifapentine granules are made by wet granulation.

16. The process of claim 15, wherein the isoniazid granules and the rifapentine granules are made by wet granulation in an aqueous solvent.

17. The process of claim 9, wherein the isoniazid granules and the rifapentine granules are made by wet granulation.

18. The process of claim 17, wherein the isoniazid granules and the rifapentine granules are made by wet granulation in an aqueous solvent.

19. The process of claim 10, wherein the isoniazid granules and the rifapentine granules are made by wet granulation.

20. The process of claim 19, wherein the isoniazid granules and the rifapentine granules are made by wet granulation in an aqueous solvent.

21. The process of claim 11, wherein the isoniazid granules and the rifapentine granules are made by wet granulation.

22. The process of claim 21, wherein the isoniazid granules and the rifapentine granules are made by wet granulation in an aqueous solvent.

* * * * *

Disclaimer

9,814,680 B2 — Prajapati Dilip, Gujarat (IN); Prasad Kum, Hyderabad (IN); Khullar Praveen, Dona Paula (IN); Kumar Ramesh, Sheohar (IN); Kumar Shakti, Paris (FR). ANTI-TUBERCULOSIS STABLE PHARMACEUTICAL COMPOSITION IN A FORM OF A DISPERSIBLE TABLET COMPRISING GRANULES OF ISONIAZID AND GRANULES OF RIFAPENTINE AND ITS PROCESS OF PREPARATION. Patent dated November 14, 2017. Disclaimer filed February 5, 2020, by the assignee, Sanofi.

Hereby disclaim complete entire claims 1-22 of said patent.

*(Official Gazette, June 9, 2020)*